United States Patent [19]
Occelli et al.

[11] 3,978,065
[45] Aug. 31, 1976

[54] RESERPINE DERIVATIVES

[75] Inventors: Emilio Occelli; Luigi Fontanella; Giangiacomo Nathansohn, all of Milan, Italy

[73] Assignee: Gruppo Lepetit S.p.A., Milan, Italy

[22] Filed: May 24, 1974

[21] Appl. No.: 473,024

[30] Foreign Application Priority Data
May 25, 1973 United Kingdom............... 25158/73

[52] U.S. Cl............................ 260/287 A; 424/262; 260/521 B
[51] Int. Cl.² ........................................ C07D 459/00
[58] Field of Search ..................... 260/287 R, 287 A

[56] References Cited
UNITED STATES PATENTS

| | | | |
|---|---|---|---|
| 2,819,271 | 1/1958 | Szmuszkovicz................. | 260/287 A |
| 2,926,167 | 2/1960 | Montmorency et al. ........ | 260/287 A |
| 2,933,499 | 4/1960 | Szmuszkovicz et al. ........ | 260/287 A |
| 2,952,682 | 9/1960 | Muller et al. ................... | 260/287 A |
| 3,109,003 | 10/1963 | Szmuszkovicz et al. ........ | 260/287 A |
| 3,126,390 | 3/1964 | Robison et al.................. | 260/287 A |

*Primary Examiner*—Alton D. Rollins
*Assistant Examiner*—David E. Wheeler
*Attorney, Agent, or Firm*—Theodore Post; C. Kenneth Bjork

[57] ABSTRACT

New reserpine-like compounds of the general formula

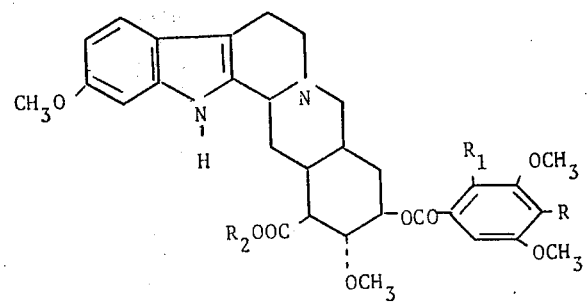

wherein R is a member of the class consisting of hydrogen, lower alkyl, lower alkenyl and acyl; $R_1$ is selected from hydrogen and lower alkyl, and $R_2$ is hydrogen or lower alkyl. The new reserpine-like compounds are useful anti-hypertensive agents.

6 Claims, No Drawings

RESERPINE DERIVATIVES

BACKGROUND OF THE INVENTION

Other reserpine-like compounds in which the carbon atoms at the 16,17 and 18 positions have the opposite steric configuration as the one occurring in natural reserpines are known from U.S. Pat. No. 3,318,877 and Belgian Pat. No. 674,186. 17α-Hydroxy reserpine derivatives are described in Belgian Pat. No. 636,674 and No. 636,675 and in Netherlands Pat. application No. 64.03268.

SUMMARY OF THE INVENTION

The present invention relates to new reserpine-like compounds. More particularly, the compounds with which the invention is concerned are reserpic acid derivatives of the following general formula I

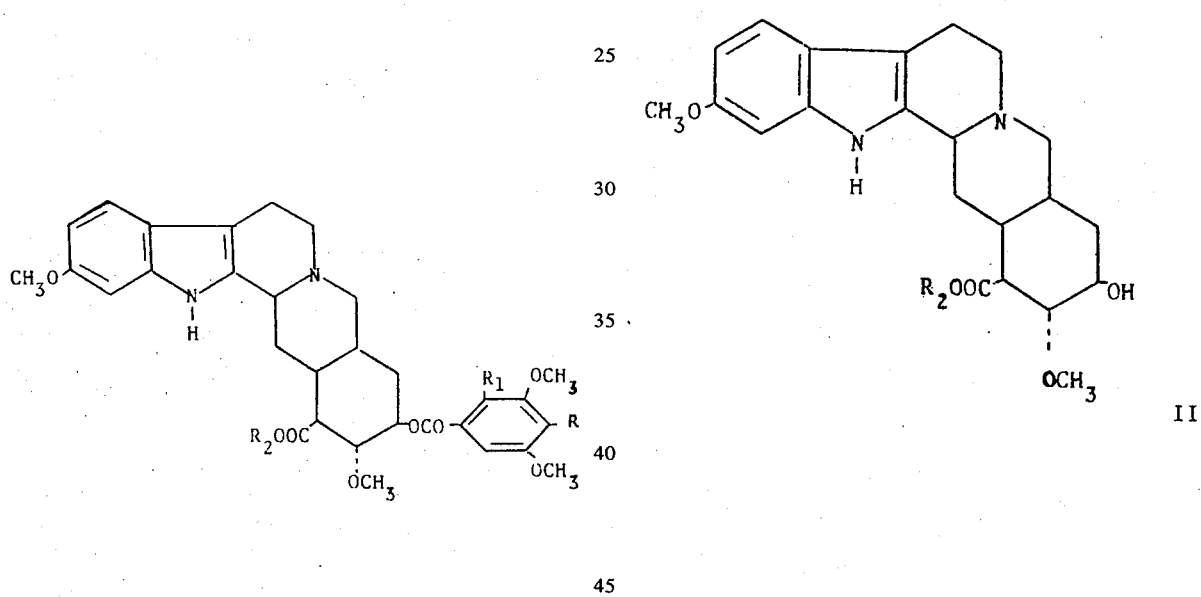

wherein R is a member of the class consisting of hydrogen, lower alkyl, lower alkenyl and acyl; $R_1$ is selected from hydrogen and lower alkyl and $R_2$ is hydrogen or lower alkyl.

As it is intended in the specification and in the claims, the terms "lower alkyl" and "lower alkenyl" refer to straight or branched alkyl and alkenyl moieties containing from 1 to 6 and from 3 to 6 carbon atoms respectively, whereas the acyl group derives essentially from a $C_2$–$C_4$ lower aliphatic carboxylic acid.

The pharmaceutically acceptable acid addition salts of the compounds of the formula I above are also included in the present invention. Such salts are essentially represented by the hydrochloride, hydrobromide, hydroiodide, sulfate, phosphate, formate, acetate, oxalate, p-toluenesulfonate, methanesulfonate, benzoate and the like, and may directly be obtained during the course of the reaction. It is obvious that, if desired, the corresponding free bases may be prepared simply by adding a suitable molecular amount of an alkali agent, e.g. an alkali metal hydroxide, to the salt. Alternatively, if the free base is directly recovered from the reaction mixture, it can be easily converted into the corresponding salt by adding a suitable molecular amount of a predetermined acid.

The general method for preparing the compounds according to the invention consists in reacting a reserpic acid derivative of the formula II with a compound of the formula III

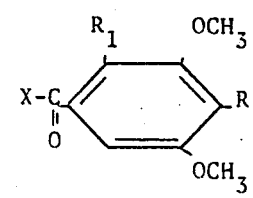

wherein R, $R_1$ and $R_2$ have the meanings given above and X may represent a halogen atom, the 1-imidazolyl radical, or a group

O-$R_3$ in which $R_3$ may be the same radical

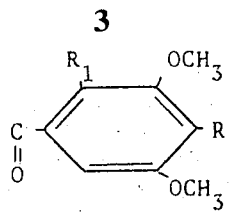

an acyl group including also trifluoroacetyl, ethoxycarbonyl or a lower alkyl-or aryl-sulfonyl moiety.

It is obvious that other useful methods for introducing the group

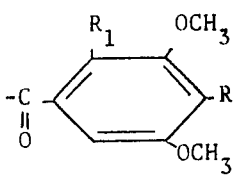

onto the desired position are intended to fall within the scope of the invention.

Generally, the reserpic acid derivative is allowed to react with a considerable excess of the compound of formula III and the condensation usually takes place in the absence of solvents.

However, when the reserpic acid derivative is contacted with a compound of the formula III wherein X is a halogen atom or a group O-$R_3$, $R_3$ being defined as above, the presence of a tertiary organic nitrogen base which is advantageously selected from pyridine, quinoline, picoline and the like, may be desired to block the inorganic or organic acid which forms during the course of the reaction and in most cases the tertiary nitrogen base may act also as the solvent.

The reaction proceeds quite smoothly at room temperature, within a range of time varying from about 10 to 45 hours, at atmospheric pressure, then the end compounds are recovered through procedures which are entirely known to a skilled chemist.

For instance, the reaction mixture, made free from any undesirable side-product by filtration, may be evaporated to dryness, and the residue taken up with an organic solvent. The evaporation of the obtained organic solution affords a residue which is further purified by recrystallization, if it is a solid, or by distillation under reduced pressure, if it is a distillable oil, or by chromatography.

The invention compounds are generally quite soluble in $C_1$–$C_4$ lower alkanols or their mixtures with water, but sparingly soluble in water. Furthermore, owing to the presence of several asymmetry centers, they are endowed also with rotatory activity.

The acyl halides of formula III and their corresponding acids are in most cases new compounds which are prepared according to methods and procedures described in the Examples.

The compounds according to the invention display good pharmacological properties. More particularly they are endowed with a considerable antihypertensive activity. The experiments to evaluate this biological action, were carried out by administering to conscious hypertensive rats effective amounts of representative members of the invention compounds. As the comparison substances, reserpine [i.e. 16β-carbomethoxy-11,17α-dimethoxy-18β-(3,4,5-trimethoxy-benzoyloxy)-yohimbane] and syrosingopine [i.e. 16β-carbomethoxy-11,17α-dimethoxy-18β-(3,5-dimethoxy-4-ethoxycarbonyloxy-benzoyloxy)-yohimbane] were tested for their antihypertensive activity, as they are widely used in the treatment of cardiovascular diseases.

The compounds of Examples 1, 3, 4, 7, 10 proved to be much more effective than the two known reserpine derivatives, as it results from the following table.

TABLE

| Compound of Example | Dose mg/Kg p.o. rats | Decrease of blood pressure mm/Hg |
| --- | --- | --- |
| 1 | 1 | − 40 |
| 3 | 0.2 | − 25 |
|   | 1 | − 50 |
| 4 | 0.2 | − 30 |
| 7 | 0.30 | − 35 |
|   | 0.50 | − 45 |
|   | 1 | − 50 |
| 10 | 0.25 | − 35 |
|   | 0.50 | − 45 |
|   | 1 | − 55 |
| Reserpine | 0.25 | − 20 |
|   | 1 | − 35 |

| Compound of Example | Dose mg/Kg p.o. rats | Decrease of blood pressure mm/Hg |
| --- | --- | --- |
| Syrosingopine | 0.5 | 0 |
|   | 1 | 0 |
|   | 10 | − 20 |
|   | 22 | − 22 |

It can be easily noticed that the compounds of the invention display a remarkable activity also at very low dosages. For instance, those of examples 4, 7 and 10 are about three to five times more active than reserpine and more than one hundred times as active as syrosingopine. Moreover, when administered in the same amount of 1 mg/Kg, the compounds of examples 1, 3, 7 and 10 cause a more marked decrease of blood pressure than reserpine.

No undesired side-effects are practically encountered when the invention compounds are administered at dosages which are effective in treating blood diseases. For instance, lachrymation, hypothermy and tremors are observed when rats are given reserpine and syrosingopine at dosages varying from about 0.3 to about 3 mg/Kg whereas the same symptoms are displayed by the invention compounds when they are administered in amounts varying from about 6 to about 10 mg/Kg, i.e. much higher than the therapeutically effective dosage.

Another favorable characteristic of the reserpine-like substances which are the object of the present invention is their scarce activity on the central nervous system.

Experiments were carried out on rats according to the Irwin scheme (S. Irwin, Psychopharmacologia (Berl.), 13, 222, 1968) and the $ED_{50}$ values effective on the following parameters i.e., spontaneous activity, motor coordination and muscular tone have been measured, said parameters being directly related to hypnotic, sedative and myorelaxing effects. In comparative tests it has been found that whereas the $ED_{50}$ values are of about 6 to 10 mg/Kg per os for reserpine, the compounds of Examples 3, 7 and 10 have influence on the above mentioned parameters only at oral dosages varying from 30 to 300 mg/Kg. This is undoubtedly a very interesting and promising pharmacological characteristic, as it may be sometimes necessary, in case of cardiovascular troubles due to hypertension, to employ a drug effective only against the specific disease, without altering the general psychic conditions of the patient.

The compounds according to the invention may be administered by various routes, e.g. orally, intravenously or intramuscularly, and are compounded into suitable pharmaceutical dosage forms in admixture with organic or inorganic, solid or liquid pharmaceutical excipients. Suitable excipients are selected from talc, propylene glycols, magnesium stearate, starch, stearyl alcohol, gums, benzyl alcohols, white petroleum jelly and the like. The pharmaceutical dosage forms may be, for example, tablets, capsules, dragees, elixirs, syrups, solutions and the like, and contain the usual preserving, stabilizing, wetting and buffering agents. These pharmaceutical preparations are prepared by conventional procedures.

DESCRIPTION OF SOME PREFERRED EMBODIMENTS

The following examples describe in details the manufacture of the compounds of the invention. They are given for the purpose of illustration only, and by no means they are intended to constitute a limitation of the scope of the invention.

EXAMPLE 1

16$\beta$-Carbomethoxy-11,17$\alpha$-dimethoxy-18$\beta$-(3,5-dimethoxy-4-methyl-benzoyloxy)-yohimbane 1 Gram (0.00242 mole) of reserpic acid methyl ester dissolved in 50 ml. of anhydrous pyridine is poured into a flask containing 2 g. (0.00930 mole) of 3,5-dimethoxy-4-methyl-benzoyl-chloride. After keeping the obtained solution at room temperature for 36 hours, 70 g. of crushed ice is added. The resulting solution is again allowed to stand at room temperature for two hours and then it is filtered. The filtrate is evaporated to dryness and the obtained residue is taken up with 50 ml. of chloroform. This organic solution is successively washed with 2% aqueous hydrochloric acid, 2% aqueous potassium hydroxide and water, then dried over sodium sulfate. The chloroform is evaporated off and after recrystallization of the residue from methanol, 0.85 g. of the title product are obtained. M.p. 236°–39°C. $[\alpha]_D$ (1%, $CHCl_3$)$^{20}$ = −127.1°

The following compounds have been prepared according to the same procedure described in Example 1.

2. — 16$\beta$-Carbomethoxy-11,17$\alpha$-dimethoxy-18$\beta$-(3,5-dimethoxy-4-ethylbenzoyloxy)-yohimbane from 1 g. (0.00242 mole) of reserpic acid methyl ester and 2 g. (0.00886 mole) of 3,5-dimethoxy-4-ethylbenzoyl chloride. Yield 1.1 g. M.p. 255°–58°C (from methanol-/acetone). $[\alpha]_D$ (0.5%, $CHCl_3$)$^{20}$ = −146°

3. — 16$\beta$-Carbomethoxy-11,17$\alpha$-dimethoxy-18$\beta$-(3,5-dimethoxy-4-propylbenzoyloxy)-yohimbane from 1 g. (0.00242 mole) of reserpic acid methyl ester and 2 g. (0.00832 mole) of 3,5-dimethoxy-4-propylbenzoyl chloride. Yield 0.9 g. M.p. 218°–21°C (from ethanol/-methanol. $[\alpha]_D$ (1%, $CHCl_3$)$^{20}$ = −115.7°

4. — 16$\beta$-Carbomethoxy-11,17$\alpha$-dimethoxy-18$\beta$-(3,5-dimethoxy-4-allyl-benzoyloxy)-yohimbane from 1 g. (0.00242 mole) of reserpic acid methyl ester and 2 g. (0.00786 mole) of 3,5-dimethoxy-4-allyl-benzoyl chloride. Yield 1 g. M.p. 206°–9°C (from methanol/-diethyl ether). $[\alpha]_D$ (1%, $CHCl_3$)$^{20}$ = −113.8°

5. — 16$\beta$-Carbomethoxy-11,17$\alpha$-dimethoxy-18$\beta$-(3,5-dimethoxy-2-propylbenzoyloxy)-yohimbane from 1 g. (0.00242 mole) of reserpic acid methyl ester and 2.25 g. (0.00926 mole) of 3,5-dimethoxy-2-propyl-benzoyl chloride. Yield 0.650 g. M.p. 184°–5°C (from methanol/water). $[\alpha]_D$ (1%, $CHCl_3$)$^{20}$ = −89°

6. — 16$\beta$-Carbomethoxy-11,17$\alpha$-dimethoxy-18$\beta$-[3,5-dimethoxy-4-(1-methyl)propyl-benzoyloxy]-yohimbane from 2.8 g. (0.00674 mole) of reserpic acid methyl ester and 4.5 g. (0.0176 mole) of 3,5-dimethoxy-4-(1-methyl)propyl-benzoyl chloride. Yield 1.9 g. M.p. 201°–3°C (from diethyl ether/light petroleum). $[\alpha]_D$ (1%, $CHCl_3$)$^{20}$ = −112°

7. — 16$\beta$-Carbomethoxy-11,17$\alpha$-dimethoxy-18$\beta$-(4-acetyl-3,5-dimethoxy)benzoyloxy-yohimbane from 2 g. (0.00483 mole) of reserpic acid methyl ester and 3 g. (0.0124 mole) of 4-acetyl-3,5-dimethoxybenzoyl chloride. Yield 1.5 g. M.p. 273°–76°C (from cool methanol). $[\alpha]_D$ (1% $CHCl_3$)$^{20}$ = −115°

8. — 16$\beta$-Carbomethoxy-11,17$\alpha$-dimethoxy-18$\beta$-(3,5-dimethoxy-4-isopropyl-benzoyloxy)-yohimbane from 3 g. (0.00725 mole) of reserpic acid methyl ester and 4 g. (0.0165 mole) of 3,5-dimethoxy-4-isopropyl-benzoyl chloride. Yield 2.2 g. M.p. 188°–90°C (from diethyl ether/light petroleum). $[\alpha]_D$ (1%, $CHCl_3$)$^{20}$ = −115.9°

9. — 16$\beta$-Carbomethoxy-11,17$\alpha$-dimethoxy-18$\beta$-(3,5-dimethoxy-4-isobutylbenzoyloxy)-yohimbane from 3 g. (0.00725 mole) of reserpic acid methyl ester and 2.2 g. (0.00860 mole) of 3,5-dimethoxy-4-isobutyl-benzoyl chloride. Yield 1.8 g. M.p. 219°–20°C (from methanol). $[\alpha]_D$ (1%, $CHCl_3$)$^{20}$ = −116.5°

10. — 16$\beta$-Carbomethoxy-11,17$\alpha$-dimethoxy-18$\beta$-(4-n-butyl-3,5-dimethoxy-benzoyloxy)-yohimbane from 4 g. (0.00967 mole) of reserpic acid methyl ester and 2.6 g. (0.0102 mole) of 4-butyl-3,5-dimethoxy-benzoyl chloride. Yield 1.7 g. M.p. 213°–15°C (from diethyl ether). $[\alpha]_D$ (1%, $CHCl_3$)$^{20}$ = −121.5°

The starting benzoyl halides were prepared according to the following procedures:

A. 3,5-Dimethoxy-4-methyl-benzoyl chloride. It is prepared as described by F. Benington et al., Journal Org. Chem. 25, 2066 (1960).

B. 3,5-Dimethoxy-4-ethyl-benzoyl chloride. Starting from 4-carbomethoxy-2,6-dimethoxy-benzoyl chloride and diethyl-malonate, and following the procedure described by H. G. Walker et al., in Journal Am.Chem.-Soc., 68, 1387 (1946), the methyl ester of 4-acetyl-3,5-dimethoxy-benzoic acid is obtained, m.p. 100°–102°C. This compound is hydrolized under alkaline conditions to the corresponding acid. (M.p. 174°–179°C from ethanol/water). The conversion of the -COCH$_3$ group at the position 4 to —CH$_2$CH$_3$ is achieved by the reductive method described by Huang Minlon in Journal Am.Chem.Soc., 68, 2487, 1946. The obtained 3,5-dimethoxy-4-ethylbenzoic acid has m.p. 190°–91°C (from methanol/water). The corresponding chloride is obtained in the same way as for the compound under A). M.p. 88°–89°C (from diethyl ether).

C. 4-Allyl-3,5-dimethoxy-benzoyl chloride. Starting from 3-hydroxy-5-methoxybenzoic acid methyl ester by reaction with allyl bromide, 3-allyloxy-5-methoxybenzoic acid methyl ester is prepared. B.p. 128°–30°C/0.4 mmHg. This compound is subjected to the allylic rearrangement performed as described by Tarbell in Organic Reactions, Vol. II, New York, 1944 and a mixture of 4-allyl-3-hydroxy-5-methoxybenzoic acid methyl ester and 2-allyl-3-hydroxy-5-methoxybenzoic acid methyl ester is obtained. By hydrolysis under alkaline conditions and separation by fractioned crystallization the pure 4-allyl-3-hydroxy-5-methoxybenzoic acid is obtained. M.p. 202°–3°C (from methanol). The reaction with dimethylsulfate according to the procedure described by F. Benington et al. in Journal Org.Chem. 25, 2066, 1960 affords the corresponding 4-allyl-3,5-dimethoxy-benzoic acid. M.p. 188°–90°C (from light petroleum). This compound is allowed to react with thionyl chloride and 4-allyl-3,5-dimethoxy-benzoyl chloride is prepared. M.p. 56°–57°C (from light petroleum).

D. 3,5-Dimethoxy-4-propyl-benzoyl chloride. 4-Allyl-3,5-dimethoxy benzoic acid is catalytically hydrogenated in the presence of $PtO_2$ to 3,5-dimethoxy-4-propyl-benzoic acid. M.p. 188°–90°C (from diethyl ether). The corresponding chloride is prepared in the same way as for the compound under A). M.p. 96°–98°C (from diethyl ether/light petroleum).

E. 3,5-Dimethoxy-2-propyl-benzoyl chloride. 2-Allyl-3-hydroxy-5-methoxybenzoic acid is obtained by fractional crystallization as described under C). M.p. 120°–22°C (from light petroleum/diethyl ether). The reaction with dimethylsulfate performed as described under C) affords the corresponding 2-allyl-3,5-dimethoxy-benzoic acid. M.p. 109°–111°C (from light petroleum/diethyl ether). This compound is catalitically hydrogenated as described under D) to 3,5-dimethoxy-2-propyl-benzoic acid. M.p. 116°–17°C (from light petroleum/diethyl ether). By reaction with thionyl chloride 3,5-dimethoxy-2-propyl-benzoyl chloride is prepared. B.p. 140°C/0.4 mm/Hg.

F. 3,5-Dimethoxy-4-(1-methyl) propyl-benzoyl chloride. Starting from 3-hydroxy-5-methoxy-benzoic acid methyl ester by reaction with 2-butenylbromide, 3-(2-butenyloxy)-5-methoxy-benzoic acid methyl ester is obtained. B.p. 156°–58°C/0.4 mmHg. By operating as described under C) the 3,5-dimethoxy-4-(3-methylpropen-3-yl)-benzoic acid is obtained. M.p. 140°–41°C (from diethyl ether/light petroleum). This compound is hydrogenated as under D) to give 3,5-dimethoxy-4-(1-methyl)propyl-benzoic acid, m.p. 125°–26°C (from diethyl ether/light petroleum). This compound is allowed to react with thionyl chloride, thus obtaining the title compound. M.p. 47°–48°C (from diethyl ether upon cooling).

G. 4-Acetyl-3,5-dimethoxy-benzoyl chloride. The preparation of the corresponding acid is described under B). The title compound is obtained through the usual reaction between acids and thionyl chloride to obtain the corresponding acyl chlorides. The title compound melts at 89°–91°C (from diethyl ether/light petroleum).

H. 3,5-Dimethoxy-4-isopropyl-benzoyl chloride. The compound prepared under G) is first reacted with aziridine according to the procedure described by D. Haidukewych et al., Tetrahedron Letters, 30, 3031-3034, 1972, obtaining 4-acetyl-3,5-dimethoxy-1-(2-oxazolinyl)-benzene, m.p. 135°–37°C (diethyl ether). This compound is reacted with magnesium methyl iodide and 2-[2,6-dimethoxy-4-(2-oxazolinyl)]-phenyl-2-propanol is obtained (m.p. 113°–16°C, from diisopropylether), from which, by treatment with sulphuric acid 3,5-dimethoxy-4-isopropenyl-benzoic acid is prepared. M.p. 169°–73°C (from ethanol/water). Said compound is hydrogenated to 3,5-dimethoxy-4-isopropyl-benzoic acid(m.p. 180°–83°C, from diethylether/light petroleum): the corresponding chloride melts at 75°–78°C (from light petroleum upon cooling).

I. 3,5-Dimethoxy-4-isobutyl-benzoyl chloride. Starting from 3-hydroxy-5-methoxy-benzoic acid methyl ester and 3-chloro-2-methyl-propene, 3-(2-methyl-2-propenyloxy)-5-methoxy-benzoic acid methyl ester is obtained. B.p. 148°–50°C/0.4 mmHg. By operating as described under C), 3,5-dimethoxy-4-(2-methylpropenyl)-benzoic acid is prepared. M.p. 159°–61°C (from diethyl ether). This compound is hydrogenated as under D) to give 3,5-dimethoxy-4-isobutyl-benzoic acid. M.p. 160°–62°C (from diethyl ether/light petroleum). The corresponding chloride melts at 48°–50°C (from ligroin upon cooling).

J. 4-Butyl-3,5-dimethoxy-benzoyl chloride. Starting from 4-carbomethoxy-2,6-dimethoxy-benzoyl chloride and the ethoxymagnesium ethyl-diethylmalonate, and operating as described under B), 4-butyryl-3,5-dimethoxy-benzoic acid is obtained. M.p. 143°–46°C (from diethyl ether/light petroleum). The conversion of the 4-butyryl to 4-butyl group is achieved as described under B) for the corresponding -$COCH_3$ group. M.p. of the 4-butyl-3,5-dimethoxybenzoic acid 173°–76°C (from diethyl ether/light petroleum). The corresponding chloride melts at 40°–42°C (from light petroleum upon cooling).

We claim:
1. A compound of the formula

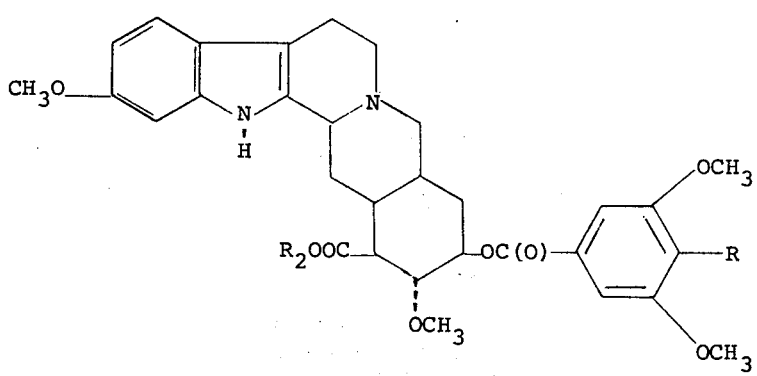

wherein R is selected from hydrogen, $C_{1-6}$ alkyl, $C_{3-6}$ alkenyl and $C_{2-4}$ alkanoyl; and $R_2$ is selected from hydrogen and $C_{1-6}$ alkyl.

2. The compound of claim 1 which is 16β-carbomethoxy-11,17α-dimethoxy-18β-(3,5-dimethoxy-4-methylbenzoyloxy)yohimbane.

3. The compound of claim 1 which is 16β-carbomethoxy-11,17α-dimethoxy-18β-3,5-dimethoxy-4-propylbenzoyloxy)yohimbane.

4. The compound of claim 1 which is 16β-carbomethoxy-11,17α-dimethoxy-18β-(4-acetyl-3,5-dimethoxybenzoyloxy)yohimbane.

5. The compound of claim 1 which is 16β-carbomethoxy-11,17α-dimethoxy-18β-(4-n-butyl-3,5-dimethoxybenzoyloxy)yohimbane.

6. The compound which is 16β-carbomethoxy-11,17α-dimethoxy-18β-(3,5-dimethoxy-4-allylbenzoyloxy)yohimbane.

* * * * *